(12) United States Patent
Donde et al.

(10) Patent No.: US 7,101,906 B2
(45) Date of Patent: Sep. 5, 2006

(54) 2,3,4-SUBSTITUTED CYCLOPENTANONES AS THERAPEUTIC AGENTS

(75) Inventors: Yariv Donde, Dana Point, CA (US); Robert M. Burk, Laguna Beach, CA (US); Michael E. Garst, Newport Beach, CA (US); Jeremiah H. Nguyen, La Puente, CA (US)

(73) Assignee: Allergan, Inc., Irvine, CA (US)

( * ) Notice: Subject to any disclaimer, the term of this patent is extended or adjusted under 35 U.S.C. 154(b) by 105 days.

(21) Appl. No.: 10/991,284

(22) Filed: Nov. 16, 2004

(65) Prior Publication Data

US 2006/0106088 A1   May 18, 2006

(51) Int. Cl.
A61K 31/881 (2006.01)
C07D 333/56 (2006.01)
C07D 333/62 (2006.01)

(52) U.S. Cl. .......................... 514/443; 549/58
(58) Field of Classification Search .................... 549/58
See application file for complete search history.

(56) References Cited

U.S. PATENT DOCUMENTS

| 4,131,738 | A |   | 12/1978 | Smith |
|---|---|---|---|---|
| 4,147,877 | A |   | 4/1979 | Smith |
| 4,154,949 | A | * | 5/1979 | Johnson et al. ............... 560/53 |
| 4,166,452 | A |   | 9/1979 | Generales |
| 4,256,108 | A |   | 3/1981 | Theeuwes |
| 4,265,874 | A |   | 5/1981 | Bonsen et al. |
| 5,703,108 | A |   | 12/1997 | Cameron et al. |
| 6,552,067 | B1 |   | 4/2003 | Cameron et al. |
| 6,586,468 | B1 |   | 7/2003 | Maruyama et al. |
| 2004/0235958 | A1 |   | 11/2004 | Yariv et al. |

FOREIGN PATENT DOCUMENTS

| DE |   | 2715838 A1 | 10/1978 |
|---|---|---|---|
| GB |   | 1601994 | 4/1978 |
| WO | WO 02/092099 |   | 11/2002 |
| WO | WO 02/102389 |   | 12/2002 |
| WO | WO 03/047513 |   | 6/2003 |

OTHER PUBLICATIONS

Chourasia and Jain in J Pharm Pharmaceut Sci 6 (1): 33-66, 2003
Remington's Pharmaceutical Sciences, Mack Publishing Company, Easton, Pa., 16th Edition, 1980.
Shareef et. al (AAPS PharmSci 2003; 5 (2) Article 17).

\* cited by examiner

*Primary Examiner*—Kamal A. Saeed
*Assistant Examiner*—Jason M. Nolan
(74) *Attorney, Agent, or Firm*—Brent A. Johnson; Robert J. Baran; Martin A. Voet

(57) ABSTRACT

Disclosed herein are compounds comprising

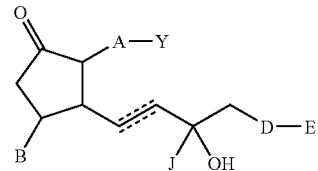

or a pharmaceutically acceptable salt or a prodrug thereof,
  wherein a dashed line represents the presence or absence of a bond;
  Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;
  A is $-(CH_2)_6-$, cis $-CH_2-CH=CH-(CH_2)_3-$, or $-CH_2-C\equiv C-(CH_2)_3-$ wherein 1 or 2 carbons may be substituted with S or O;
  B is hydrogen, $C_{1-6}$ hydrocarbyl, CN, $CO_2H$, or $-(CH_2)_m X(CH_2)_p H$, wherein m is at least 1 and the sum of m and p is from 1 to 5;
  X is S or O;
  J is H, $CH_3$, or $CF_3$;
  D is a covalent bond, $CH_2$, O, or S; and
  E is an aromatic heterobicyclic ring system which may have substituents comprising up to 6 non-hydrogen atoms each.

Figure 1:
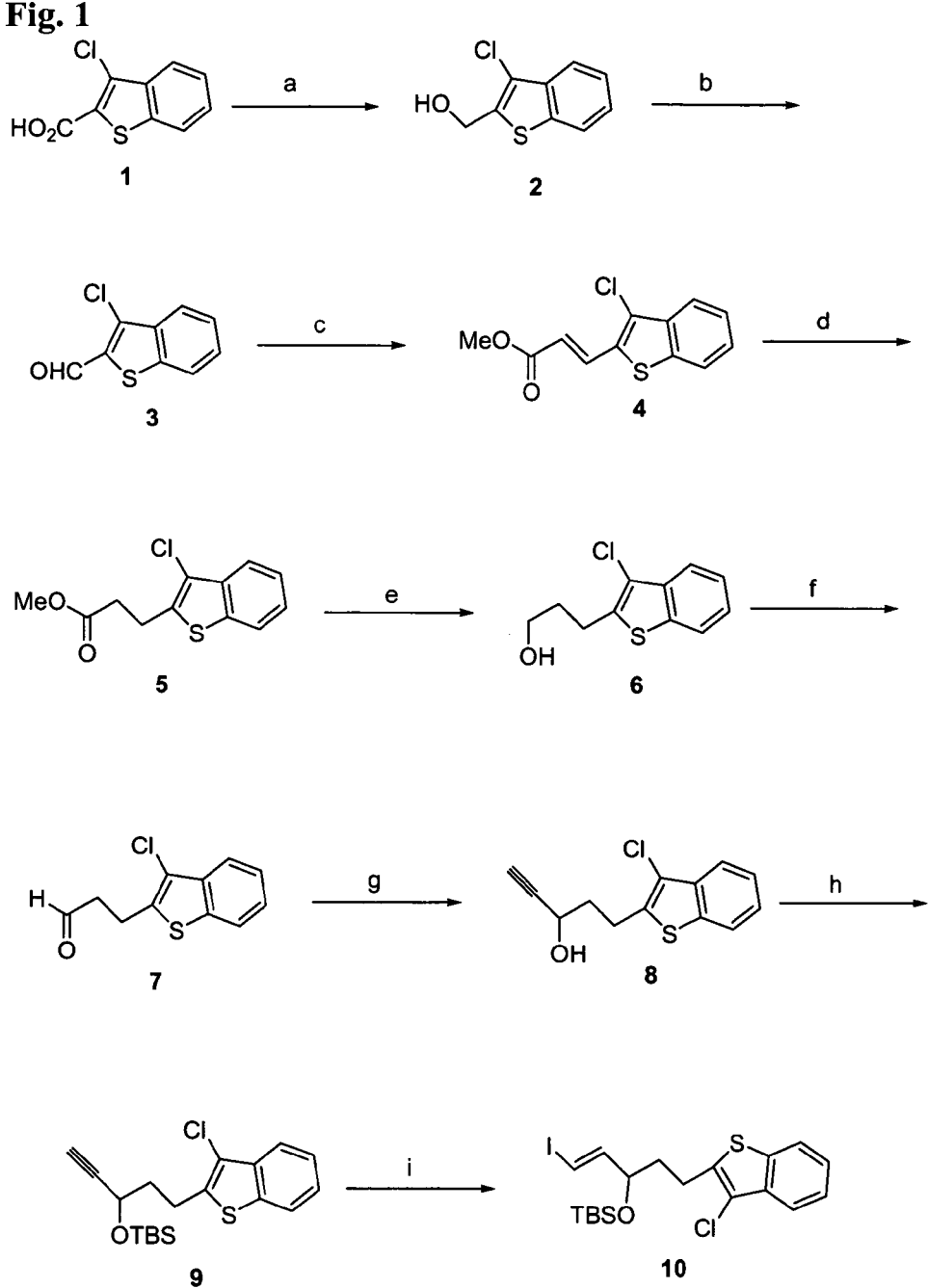

Methods, compositions, and medicaments related thereto are also disclosed.

24 Claims, 5 Drawing Sheets

(a) LiAlH$_4$; (b) TPAP, NMO; (c) Ph$_3$P=CHCO$_2$Me; (d) (Ph$_3$P)$_3$RhCl, H$_2$; (e) LiBH$_4$;
(f) Swern [O]; (g) ethynylmagnesium bromide; (h) TBSCl, DMAP, Et$_3$N; (i) Cp$_2$ZrHCl; NIS.

(a) t-BuLi, THF -78 °C; 2-ThienylCuCNLi, THF -78 °C; (b) enone, THF -78 °C; (c) HOAc, H$_2$O,THF 70 ° C; (d) TBSOTf, 2,6-lutidine, CH$_2$Cl$_2$; (e) [Ph$_3$PCuH]$_6$, Me$_2$CuLi or RCuMgBr; (f) HF-pyridine, CH$_3$CN; (g) 0.5 M LiOH, THF; (h) DBU, 2-iodopropane.

(a) TBSCl, etc.; (b) n-BuLi; DMF; (c) Ac$_2$O, pyridine; (d) Jones oxidation; (e) MeOH, AcCl; (f) PPh$_3$, I$_2$, imidazole, CH$_2$Cl$_2$.

(a) *t*-BuLi, THF -78 °C; (b) Me$_2$Zn; (c) HF-pyridine, CH$_3$CN; separate diastereomers; (d) NiCl$_2$, NaBH$_4$, ethylenediamine, H$_2$; (e) rabbit liver esterase, pH 7.2 phosphate buffer, CH$_3$CN.

low Rf + high Rf diastereomers

R = CH₃, 38, 39
R = H, 40, 41

(a) *n*-BuLi; ethylene oxide; (b) Dess-Martin [O]; (c) ethynylmagnesium bromide; (d) TBSCl, DMAP, Et₃N; (e) Cp₂ZrHCl; NIS.

2,3,4-SUBSTITUTED CYCLOPENTANONES AS THERAPEUTIC AGENTS

FIELD OF THE INVENTION

This invention relates to therapeutically active agents. Particularly this invention relates to compounds which are prostaglandin or prostamide receptor agonists.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

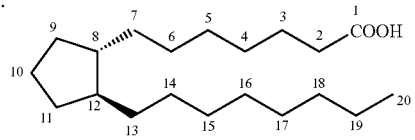

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

U.S. Pat. No. 4,131,738 and U.S. Pat. No. 4,147,877 disclose certain 6-hydroxy, 11-dihydro and 11 hydroxymethyl prostaglandin E derivatives.

British patent 1601994 discloses certain 11-dihydro and 11-alkyl prostaglandin E derivatives.

Prostaglandin $EP_4$ selective agonists are believed to have several medical uses. For example, U.S. Pat. No. 6,552,067 B2 teaches the use of prostaglandin EP4 selective agonists for the treatment of "methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal".

U.S. Pat. No. 6,586,468 B1 teaches that prostaglandin EP4 selective agonists "are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colitis, Crohn's diseases, hypercytokinemia at dialysis, multiple organ failure, shock, etc. They are also connected with sleeping disorders and platelet coagulations, and therefore they are thought to be useful for these diseases."

Inflammatory bowel disease (IBD) is a group of disease characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "EP4 works to keep mucosal integrity, to suppress the innate immunity, and to downregulate the proliferation and activation of CD4+ T cells. These findings have not only elucidated the mechanisms of IBD by NSAIDs, but also indicated the therapeutic potential of EP4-selective agonists in prevention and treatment of IBD." (Kabashima, et. al., The Journal of Clinical Investigation, April 2002, Vol. 9, 883–893)

BRIEF DESCRIPTION OF THE INVENTION

Disclosed herein are compounds comprising

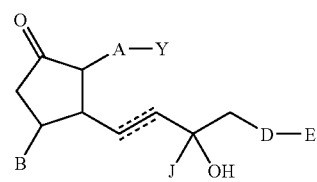

or a pharmaceutically acceptable salt or a prodrug thereof, wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_6-$, cis $-CH_2-CH=CH-(CH_2)_3-$, or $-CH_2-C\equiv C-(CH_2)_3-$ wherein 1 or 2 carbons may be substituted with S or O;

B is hydrogen, $C_{1-6}$ hydrocarbyl, CN, $CO_2H$, or $-(CH_2)_m X(CH_2)_p H$, wherein m is at least 1 and the sum of m and p is from 1 to 5;

X is S or O;

J is H, $CH_3$, or $CF_3$;

D is a covalent bond, $CH_2$, O, or S; and

E is an aromatic heterobicyclic ring system which may have substituents comprising up to 6 non-hydrogen atoms each.

Methods, compositions, and medicaments related thereto are also disclosed.

BRIEF DESCRIPTION OF THE DRAWING FIGURES

Figure 2:
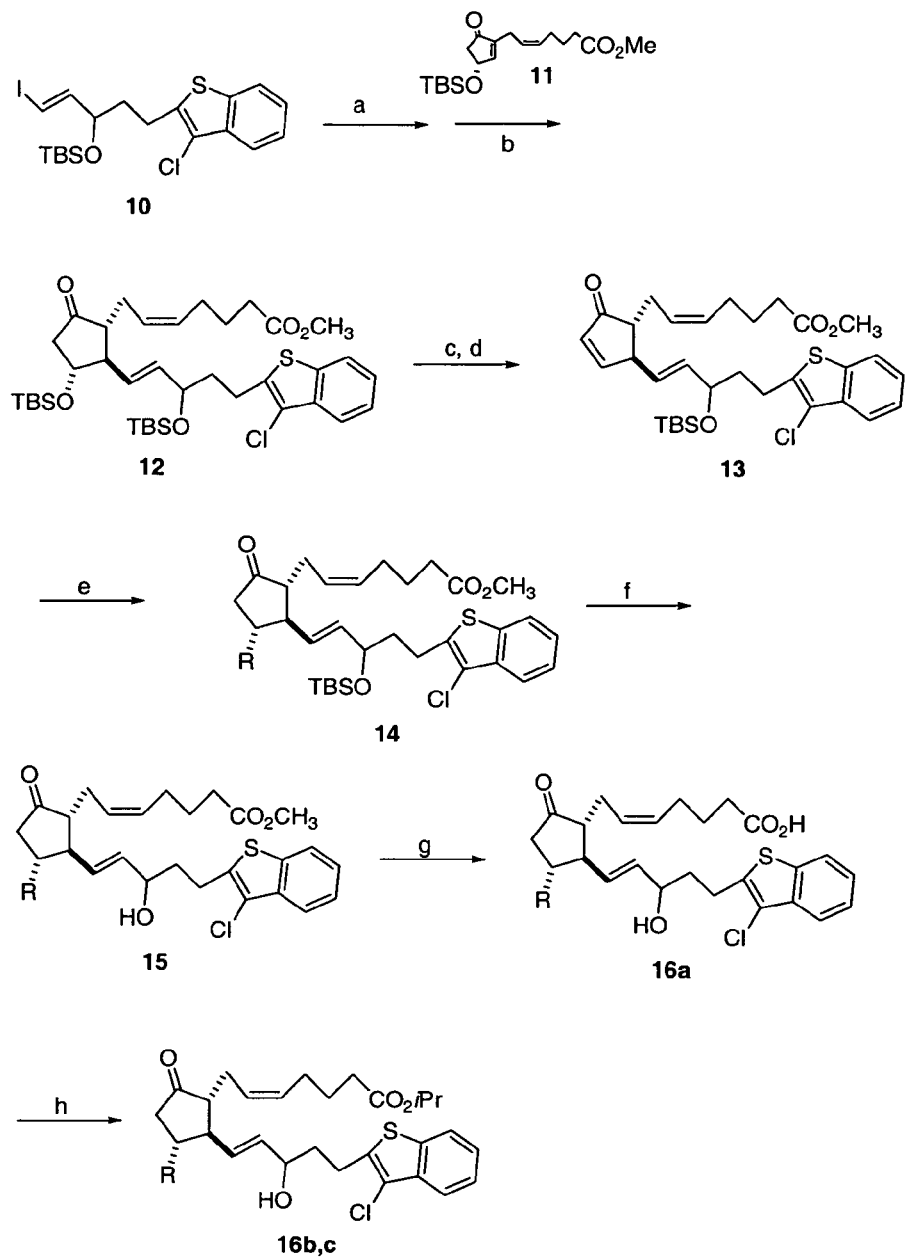
Figure 3:
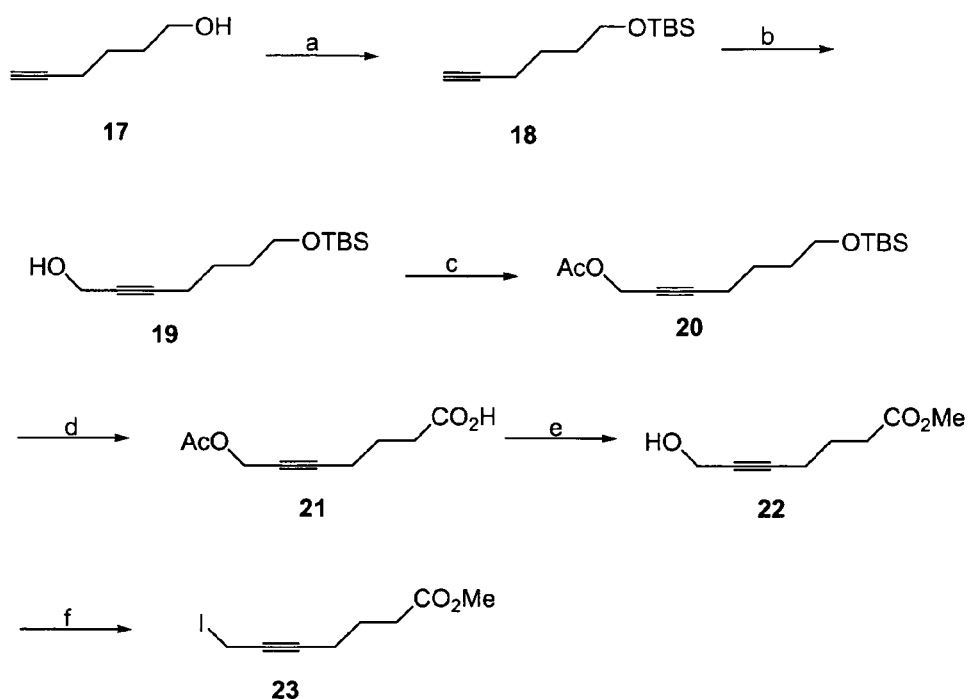
Figure 4:
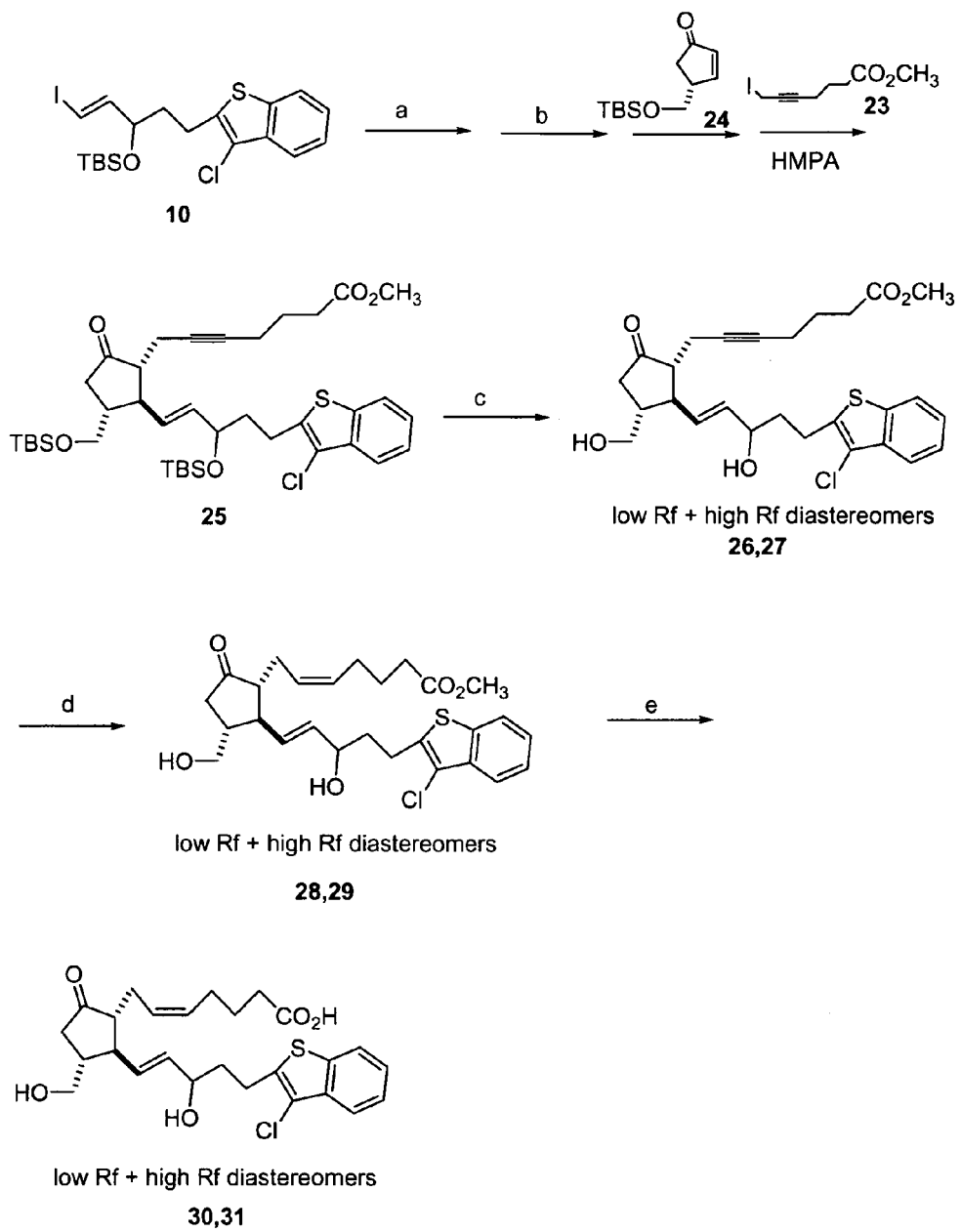
Figure 5:
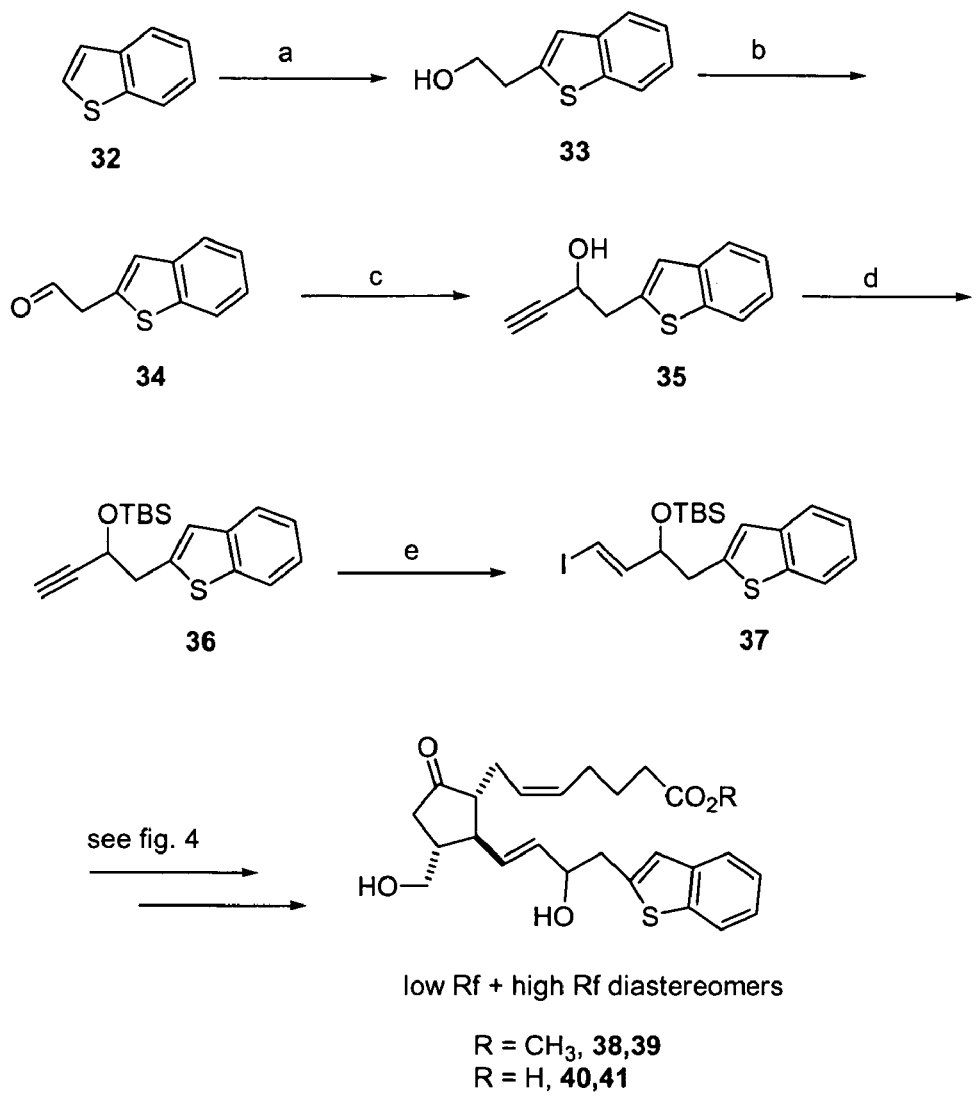

FIGS. 1–5 demonstrate one method of preparing the compounds disclosed herein.

DETAILED DESCRIPTION OF THE INVENTION

In all of the structures shown herein, a dashed line represents the presence or absence of a bond. In other words, for a structure such as the one shown below:

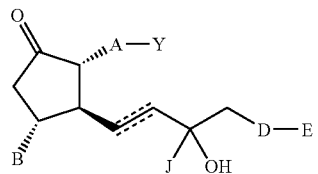

any of the following structures are possible.

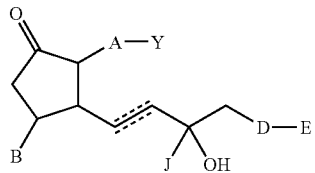

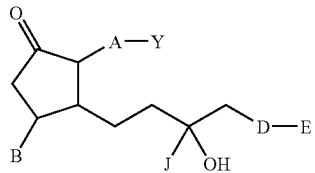

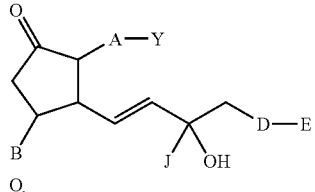

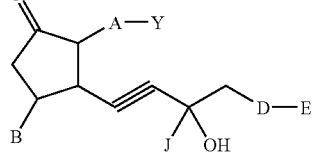

Pharmaceutically acceptable salts or prodrugs of compounds represented by the foregoing structures are also contemplated.

There are several stereocenters in the compounds disclosed herein. While not intending to limit the scope of the invention in any way, compounds having the stereochemistry shown below are of special interest.

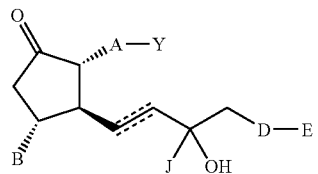

Additionally, it is useful for one or more of the bonds to have the stereochemistry indicated, such as in the structures shown below.

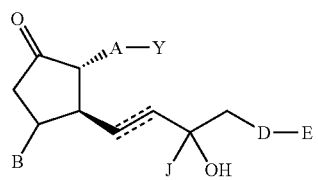

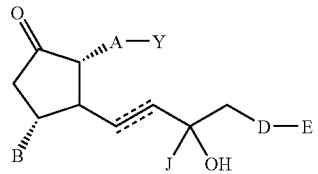

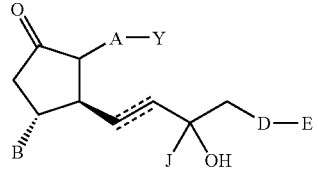

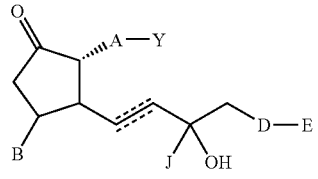

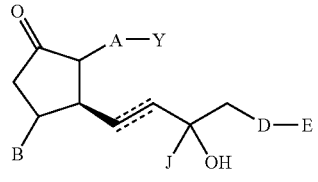

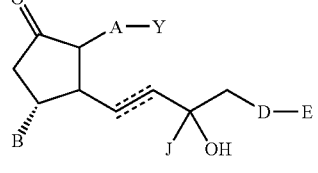

As with any structure disclosed herein, pharmaceutically acceptable salts or prodrugs of compounds represent by the above structures are also contemplated.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line," "represents a bond receding from the viewer."

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group. Thus, while not intending to limit the scope of the invention in any way, in certain compounds Y is a carboxylic acid, sulfonic acid, or phosphonic acid functional group, i.e. one of the structures shown below.

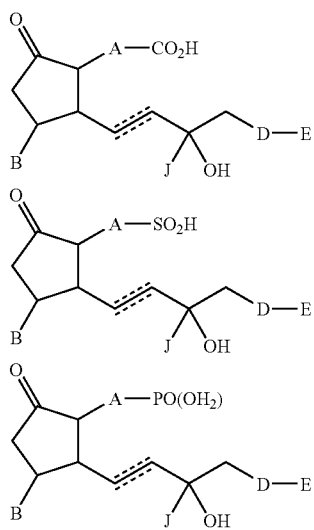

Salts of any of these acids of any pharmaceutically acceptable form are also possible.

Additionally, an amide or ester of one of the organic acids shown above comprising from 0 to 12 carbon atoms is also contemplated. In an ester, a hydrocarbyl moiety replaces a hydrogen of an acid such as in a carboxylic acid ester, e.g. $CO_2R^2$. In an amide, an amine group replaces an OH of the acid. An amine is a moiety with a central nitrogen that has exactly three bonds to C or H. Examples of amides include $CON(R^2)_2$, $CON(OR^2)R^2$, $CON(CH_2CH_2OH)_2$, and $CONH(CH_2CH_2OH)$. Moieties such as $CONHSO_2R^2$ are also amides of the carboxylic acid notwithstanding the fact that they may also be considered to be amides of the sulfonic acid $R^2$—$SO_3H$.

While not intending to limit the scope of the invention in any way, Y may also be hydroxymethyl or an ether thereof comprising from 0 to 12 carbon atoms. Thus, compounds having a structure shown below are possible.

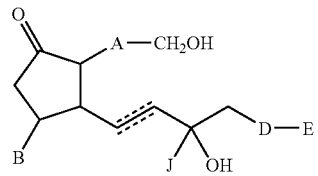

Additionally, ethers of these compounds are also possible. An ether is defined as a functional group wherein a hydrogen of an hydroxyl is replaced by carbon, e.g., Y is $CH_2OCH_3$, $CH_2OCH_2CH_3$, etc.

Finally, while not intending to limit the scope of the invention in any way, Y may be a tetrazolyl functional group, i.e. compounds having a structure such as one of those shown below.

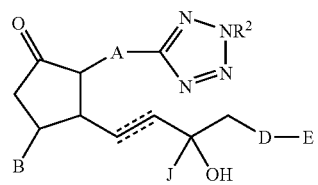

When $R^2$ is hydrogen, the tetrazolyl functional group has two tautomeric forms, which can rapidly interconvert in aqueous or biological media, and are thus equivalent to one another. These tautomers are shown below.

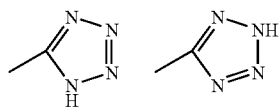

Additionally, if $R^2$ is $C_1$–$C_6$ alkyl, phenyl, or biphenyl, other isomeric forms of the tetrazolyl functional group such as the one shown below are also possible, all of these are considered to be within the scope of the term "tetrazolyl."

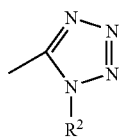

While not intending to limit the scope of the invention in any way, in one embodiment, Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and tetrazolyl-$R^2$;

wherein $R^2$ is independently H, $C_1$–$C_6$ alkyl, phenyl, or biphenyl.

In relation to the identity of A disclosed in the chemical structures presented herein, in the broadest sense, A is —$(CH_2)_6$—, cis —$CH_2CH$═$CH$—$(CH_2)_3$—, or —$CH_2C$≡$C$—$(CH_2)_3$—, wherein 1 or 2 carbon atoms may be substituted with S or O. In other words, in certain embodiments, A is —$(CH_2)_6$—, in other embodiments, A is cis —$CH_2CH$═$CH$—$(CH_2)_3$—, in other embodiments, A is —CH$_2$CH=CH—(CH$_2$)$_3$—, or A may be a group which is related to one of these three moieties in that any carbon is substituted with S or O. For example, while not intending to limit the scope of the invention in any way, in certain embodiments A is an S substituted moiety such as one of the following or the like.

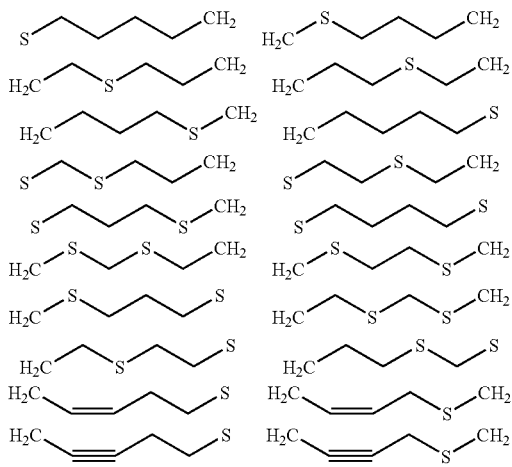

Alternatively, while not intending to limit the scope of the invention in any way, A may be an O substituted moiety such as one of the following or the like.

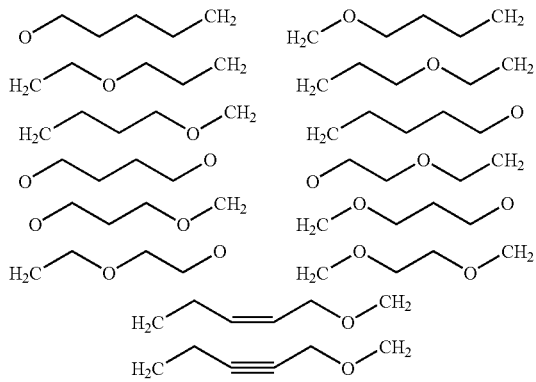

Alternatively, while not intending to limit the scope of the invention in any way, A may have both an O and an S substituted in the chain, such as one of the following or the like.

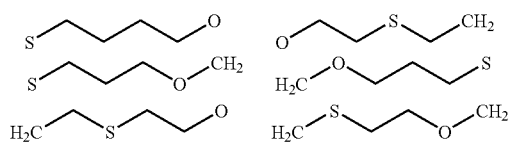

B is hydrogen, C$_{1-6}$ hydrocarbyl, CN, CO$_2$H, or —(CH$_2$)$_m$X(CH$_2$)$_p$H, wherein m is at least 1 and the sum of m and p is from 1 to 5. Hydrocarbyl is a moiety having only carbon and hydrogen such as C$_{1-6}$ alkyl including methyl, ethyl, and the like; C$_{2-6}$ alkenyl such as ethenyl or the like; C$_{2-6}$ alkynyl; phenyl; or the like. Alkyl is hydrocarbyl having no double or triple bonds, which may be linear, such as n-butyl; cyclic, such as cyclobutyl; branched, such as t-butyl; or any combination thereof. Alkenyl should be broadly understood to be hydrocarbyl having one or more C=C bonds but no triple bonds, which may be linear, branched, cyclic, or a combination thereof. While not intending to be limiting, typical examples are ethenyl, propenyl, butadienyl; cyclopentenyl; and the like. Alkynyl should be broadly understood to be hydrocarbyl having one or more C≡C bonds such as ethynyl, propynyl; butadiynyl; and the like. Combinations of any of the above are also possible.

While not intending to be limiting, in one embodiment, B is hydrocarbyl having from 1 to 4 carbon atoms. In another embodiment, B is hydrocarbyl having from 1 to 3 carbon atoms. In other embodiments, B is alkyl having from 1–3 carbon atoms. In other embodiments, B is alkylene having from 2–3 carbon atoms.

Alternatively, B may be —(CH$_2$)$_m$X(CH$_2$)$_p$H, wherein m is at least 1 and the sum of m and p is from 1 to 5, and X is S or O; i.e. there are from 1 to 5 methylene (CH$_2$) groups and an S or an O atom. Thus, B may be an ethereal moiety having from 1 to 5 carbon atoms such as —CH$_2$OCH$_3$, —CH$_2$CH$_2$OCH$_3$, etc.; or a hydroxyalkyl having from one to five carbon atoms such as hydroxymethyl (—CH$_2$OH), hydroxyethyl, etc. Sulfur containing analogs are also possible, i.e. where X is S. In one embodiment, the sum of m and p is from 1 to 3.

J is H, CH$_3$, or CF$_3$. In other words, while not intending to limit the scope of the invention in any way, compounds represented by the structural formula below are possible.

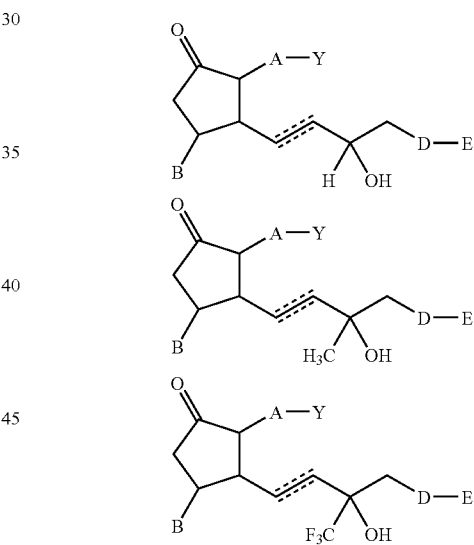

As with any structure disclosed herein, pharmaceutically acceptable salts or prodrugs of compounds represent by the above structures are also contemplated.

D is a covalent bond, CH$_2$, O, or S. Thus, while not intending to be limiting, compounds of the following structures are also contemplated.

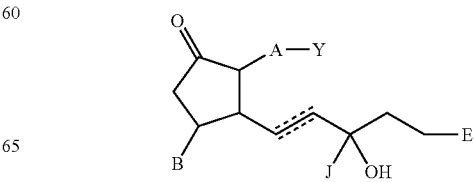

-continued

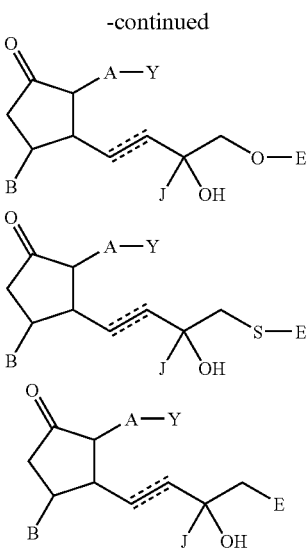

As with any structure disclosed herein, pharmaceutically acceptable salts or prodrugs of compounds represent by the above structures are also contemplated.

While not intending to limit the scope of the invention in any way, in certain embodiments D is $CH_2$. In other embodiments, D is S or O.

E is an aromatic heterobicyclic ring system which may have substituents comprising up to 6 non-hydrogen atoms each. In other words, E is a bicyclic ring system which has an aromatic ring in it. While not intending to limit the scope of the invention in any way, only one of the two rings need be aromatic, such as in for example, 2,2,4,4-tetrahydrobenzofuryl. Alternatively, both rings in the system may be aromatic. Examples of such ring systems include, but are not limited to, ring systems with one heteroatom and ring systems with more than one heteroatom. Ring systems with one heteroatom include those having a sulfur atom such as benzothienyl and isobenzothienyl; those having an oxygen atom such as benzofuryl and isobenzofuryl; and those having a nitrogen atom such as quinolinyl, isoquinolinyl, indolyl, isobenzofuryl, isondolyl, benzopyridyl, and the like. Ring systems with more than one heteroatom include moieties such as benzimidazolyl, benzothiazolyl, benzopyrimidyl, benzopyrazinyl, and the like.

The ring systems of E may be unsubstituted, or they may have up to as many substituents as the ring system will bear. Thus, for example, benzothienyl, isobenzothienyl, benzofuryl, and isobenzylfuryl may have up to four substituents. The substituents comprise up to 6 non-hydrogen atoms each. In other words, the substituent will have up to 6 atoms which are not hydrogen, including C, N, S, O, P, F, Cl, Br, I, etc., and will have any number of hydrogen atoms required by the circumstances. Thus, while not intending to limit the scope of the invention in any way, the substituents may include hydrocarbyl up to $C_6$ such as alkyl, alkylenyl, alkynyl, and the like, whether linear, branched, cyclic, or a combination thereof; hydrocarbyloxy up to $C_5$ such as methoxy, ethoxy, and the like; acyl up to $C_5$; acyloxy up to $C_4$; $CO_2H$ and salts; $SO_3H$ and salts; $PO(OH)_2$ and salts; sulfonyl up to $C_3$, phosphonyl up to $C_3$; $NO_2$; CN; halogens such as fluoro, chloro, and bromo; fluorocarbyl such as $CF_3$; amines up to C5; and the like. A counterion of a salt is not counted as part of a substituent. For example, $CO_2^-Na^+$ is considered to have 3 non-hydrogen atoms since $Na^+$ is not counted. If more than one substituent is present, they may be identical or present in any combination.

While not intending to be limiting, in one embodiment E has from 0 to 3 substituents, wherein the substituents comprise no more than 4 non-hydrogen atoms each. Thus, the substituents may include hydrocarbyl up to $C_4$, such as methyl, ethyl, etc; hydrocarbyloxy up to $C_3$ such as methoxy, ethoxy, etc; acyl up to $C_3$; acyloxy up to $C_2$; $CO_2H$ and salts; $SO_3H$ and salts; $PO(OH)_2$ and salts; sulfonyl up to $C_2$; phosphonyl up to $C_2$; halogen; CN; $NO_2$; $CF_3$; and the like. In particular, methyl, ethyl, isopropy, methoxy, fluoro, chloro, bromo, and trifluoromethyl, are useful as substituents for E.

In one embodiment, E is a monosubstituted aromatic heterobicyclic ring system. In another embodiment, E is monosubstituted benzothienyl. In another embodiment E is benzothienyl having from 0 to 3 substituents, said substituents comprising no more than 4 non-hydrogen atoms each. In another embodiment, E is substituted in the 3-position. In another embodiment, E is 3-chloro-2-benzothienyl.

Compounds represented by the structure below are specifically contemplated herein.

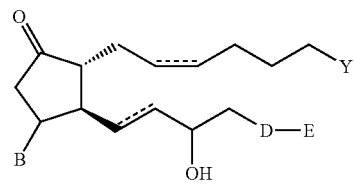

Thus, any of the structures shown below are possible.

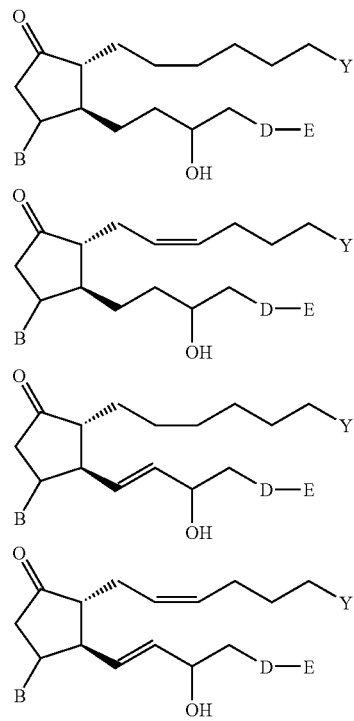

As with any structure disclosed herein, pharmaceutically acceptable salts or prodrugs of compounds represent by the above structures are also contemplated.

While not intending to be limiting, compounds represented by the structure below are specifically contemplated herein.

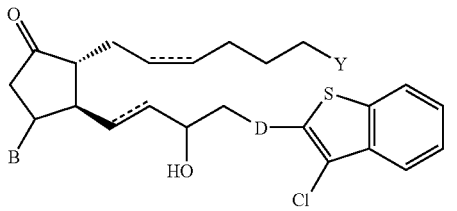

Thus, any of the structures shown below are possible.

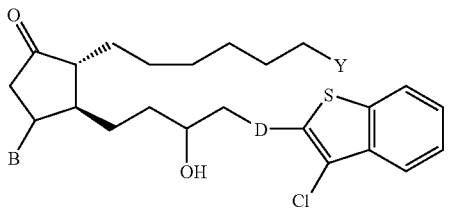

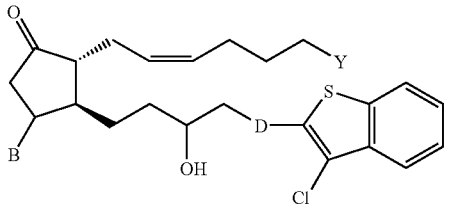

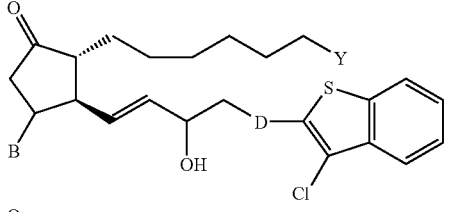

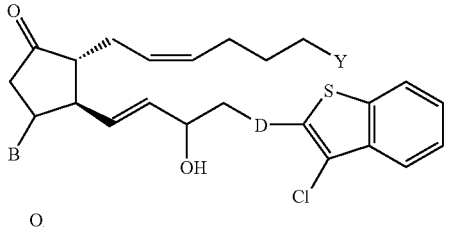

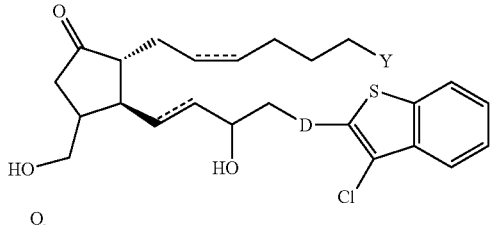

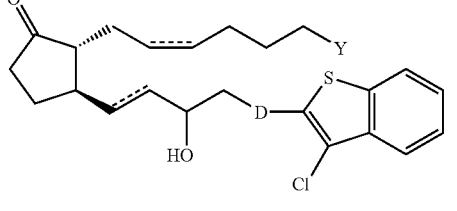

As with any structure disclosed herein, pharmaceutically acceptable salts or prodrugs of compounds represent by the above structures are also contemplated.

While not intending to be limiting, the following compounds are also specifically contemplated herein.

(Z)-7-{(1R,2R,3R)-2-[(E)-5-(3-Chloro-benzo[b]thiophen-2-yl)-3-hydroxy-pent-1-enyl]-3-ethyl-5-oxo-cyclopentyl}-hept-5-enoic acid methyl ester;

(Z)-7-{(1R,2R,3R)-2-[(E)-5-(3-Chloro-benzo[b]thiophen-2-yl)-3-hydroxy-pent-1-enyl]-3-ethyl-5-oxo-cyclopentyl}-hept-5-enoic acid;

7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-ynoic acid methyl ester;

(Z)-7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-enoic acid methyl ester;

(Z)-7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-enoic acid;

(Z)-7-{(1R,2S,3S)-2-[(E)-5-(3-Chloro-benzo[b]thiophen-2-yl)-3-hydroxy-pent-1-enyl]-3-isopropyl-5-oxo-cyclopentyl}-hept-5-enoic acid methyl ester;

(Z)-7-{(1R,2R,3R)-2-[(E)-5-(3-Chloro-benzo[b]thiophen-2-yl)-3-hydroxy-pent-1-enyl]-3-methyl-5-oxo-cyclopentyl}-hept-5-enoic acid methyl ester;

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid methyl ester;

(Z)-7-{(1R,2S,3S)-2-[(E)-5-(3-Chloro-benzo[b]thiophen-2-yl)-3-hydroxy-pent-1-enyl]-5-oxo-3-vinyl-cyclopentyl}-hept-5-enoic acid methyl ester;

(Z)-7-{(1R,2S,3 S)-2-[(E)-5-(3-Chloro-benzo[b]thiophen-2-yl)-3-hydroxy-pent-1-enyl]-3-isopropyl-5-oxo-cyclopentyl}-hept-5-enoic acid;

(Z)-7-{(1R,2R,3R)-2-[(E)-5-(3-Chloro-benzo[b]thiophen-2-yl)-3-hydroxy-pent-1-enyl]-3-methyl-5-oxo-cyclopentyl}-hept-5-enoic acid;

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid;

(Z)-7-{(1R,2S,3S)-2-[(E)-5-(3-Chloro-benzo[b]thiophen-2-yl)-3-hydroxy-pent-1-enyl]-5-oxo-3-vinyl-cyclopentyl}-hept-5-enoic acid;

(Z)-7-[(1R,2S,3R)-2-((E)-4-Benzo[b]thiophen-2-yl-3-hydroxy-but-1-enyl)-3-hydroxymethyl-5-oxo-cyclopentyl]-hept-5-enoic acid methyl ester;

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid isopropyl ester; and (Z)-7-[(1R,2S,3R)-2-((E)-4-Benzo[b]thiophen-2-yl-3-hydroxy-but-1-enyl)-3-hydroxymethyl-5-oxo-cyclopentyl]-hept-5-enoic acid.

The compounds disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_4$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1–6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33–66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid humans in clinical trials for the treatment of irritable bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

Biological Activity

The activity of compounds disclosed herein was tested according to the following procedures. The results are presented in Table 1.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour. Non-specific binding was determined with 10 uM unlabeled 17-phenyl $PGF_{2\alpha}$.

[$^3$H-] $PGE_2$ (5 nM; specific activity 180 Ci mmol) was used as the radioligand for EP receptors. Binding studies employing $EP_1$, $EP_2$, $EP_3$, $EP_4$ were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Non-specific binding determined with $10^{-5}$M of unlabeled PGE$_2$.

Methods For FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3.4}$/Gqi5; hEP$_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_3$A/Gqi5; hEP4/Gqs5); PGF$_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

TABLE 1

| STRUCTURE | Stereo Chem | Binding IC$_{50}$ (nM) | | | Functional EC$_{50}$ (nM) | | | | | | |
|---|---|---|---|---|---|---|---|---|---|---|---|
| | | HEP2 | HEP3D | HEP4 | HFP | HEP1 | HEP2 | HEP3A | HEP4 | HTP | HIP | HDP |
| (structure 1) | 1:1 diast. | NA | 1800 | NA | >10K | NA | >10K | 153 | NA | NA | NA | |
| (structure 2) | 1:1 diast. | NA | >10K | NA | NA | NA | NA | >10K | NA | NA | NA | |
| (structure 3) | 1:1 diast. | NA | >10K | NA | NA | NA | NA | NA | NA | NA | NA | |

TABLE 1-continued
| STRUCTURE | Stereo Chem | Binding IC$_{50}$ (nM) | | | Functional EC$_{50}$ (nM) | | | | | | | |
|---|---|---|---|---|---|---|---|---|---|---|---|---|
| | | HEP2 | HEP3D | HEP4 | HFP | HEP1 | HEP2 | HEP3A | HEP4 | HTP | HIP | HDP |
| 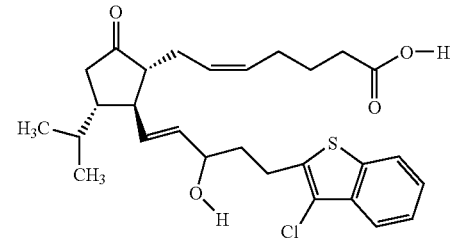 | 1:1 diast. | NA | >10K | NA | NA | NA | NA | >10K | NA | NA | NA | |
| 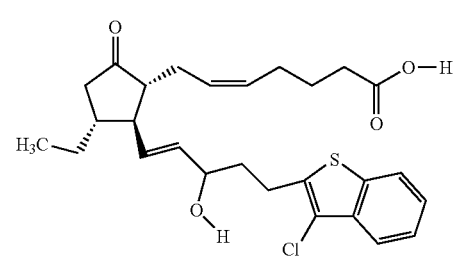 | 1:1 diast. | NA | 2100 | NA | NA | | | 708 | | | | |
| 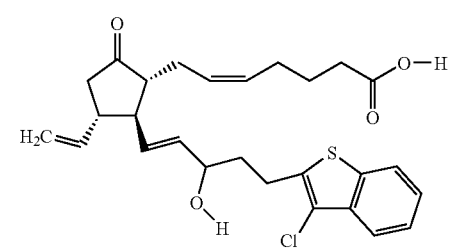 | 1:1 diast. | >10K | 650 | NA | NA | | | 156 | | | | |
| 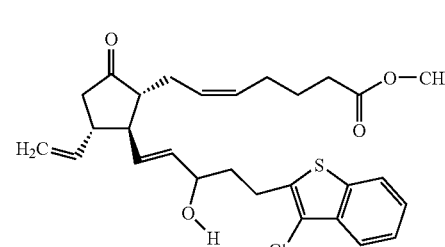 | 1:1 diast. | NA | >10K | NA | NA | | | 1698 | | | | |
| 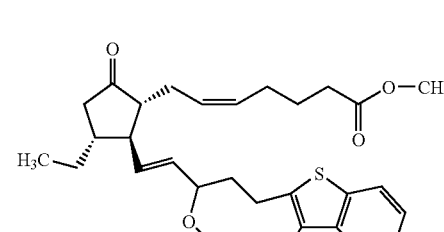 | 1:1 diast. | NA | >10K | NA | NA | | | NA | | | | |

TABLE 1-continued

| STRUCTURE | Stereo Chem | Binding IC$_{50}$ (nM) | | | Functional EC$_{50}$ (nM) | | | | | | | |
|---|---|---|---|---|---|---|---|---|---|---|---|---|
| | | HEP2 | HEP3D | HEP4 | HFP | HEP1 | HEP2 | HEP3A | HEP4 | HTP | HIP | HDP |
| 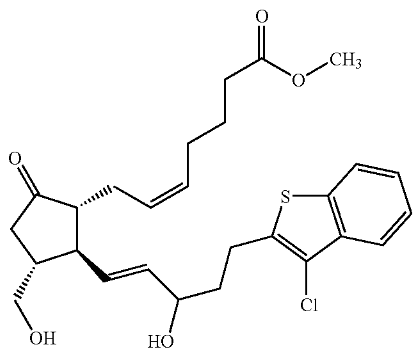 | High Rf diast. | | | | NA | NA | NA | NA | >10K | NA | NA | NA |
| | Low Rf diast. | | | | NA | NA | NA | NA | >10K | NA | NA | NA |
| 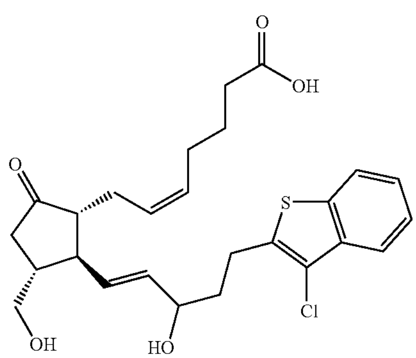 | High Rf diast | | | | NA | NA | NA | NA | 1245 | NA | NA | NA |
| | Low Rf diast. | | | | NA | NA | NA | NA | 1786 | NA | NA | NA |

TABLE 1-continued

| STRUCTURE | Stereo Chem | Binding IC$_{50}$ (nM) | | | Functional EC$_{50}$ (nM) | | | | | | | |
|---|---|---|---|---|---|---|---|---|---|---|---|---|
| | | HEP2 | HEP3D | HEP4 | HFP | HEP1 | HEP2 | HEP3A | HEP4 | HTP | HIP | HDP |
| | High Rf diast. | | | | NA | >10K | NA | NA | >10K | >10K | NA | NA |
| | Low Rf diast | | | | NA | >10K | >10K | 9000 | >10K | >10K | NA | NA |
| | High Rf diast. | | | | NA | >10K | >10K | >10K | >10K | >10K | NA | NA |
| | Low Rf Diast | | | | NA | 9 | >10K | 99 | 1770 | | NA | NA |
| 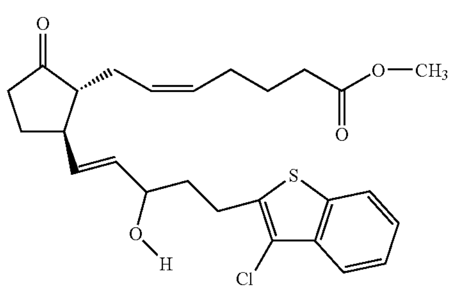 | High Rf diast | | | | NA | NA | NA | NA | 515 | NA | NA | NA |

TABLE 1-continued

| STRUCTURE | Stereo Chem | Binding IC$_{50}$ (nM) | | | Functional EC$_{50}$ (nM) | | | | | | | |
|---|---|---|---|---|---|---|---|---|---|---|---|---|
| | | HEP2 | HEP3D | HEP4 | HFP | HEP1 | HEP2 | HEP3A | HEP4 | HTP | HIP | HDP |
| | Low Rf diast | | | | NA | NA | NA | NA | 862 | >10K | NA | NA |
| | High Rf diast | >10K | 6000 | 150 | NA | NA | NA | NA | 11 | NA | NA | NA |
| | Low Rf diast. | NA | 3700 | 110 | NA | NA | NA | >10K | 25 | >10K | NA | NA |
| | High Rf diast | | | | | | | | | | | |
| | Low Rf diast | | | | | | | | | | | |

In Vivo Testing

Intraocular Pressure (IOP)

Intraocular pressure studies in dogs involved pneumatonometry performed in conscious, Beagle dogs of both sexes (10–15 kg). The animals remained conscious throughout the study and were gently restrained by hand. Drugs were administered topically to one eye as a 25 µL volume drop, the other eye received 25 µL vehicle (0.1% polysorbate 80:10 mM TRIS) as a control. Proparacaine (0.1%) was used for corneal anesthesia during tonometry.

Intraocular pressure was determined just before drug administration and at 2, 4 and 6 hr thereafter on each day of the 5 day study. Drug was administered immediately after the first IOP reading.

An analogous procedure was carried out with cynomolgus monkeys with measurements at 2, 4, 6, and 24 hours after a single dose.

Pupil Diameter

Dog pupil diameter was measured using an optistick (a mm ruler which included half-circle references of standard widths (mm) for reference. Gently restraining the dog by hand, pupil diameter was determined by matching a half-circle to the pupil in normal room light. In dogs with very dark pupils a specialized penlight was used, but only very briefly to avoid pupil constriction. Pupil diameter was measured at the same time as IOP and hyperemia.

Ocular Surface Hyperemia

Ocular surface hyperemia was visually assessed and scored according to a system typically used clinically.

| Hyperemia Score | Assigned Value |
| --- | --- |
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range.

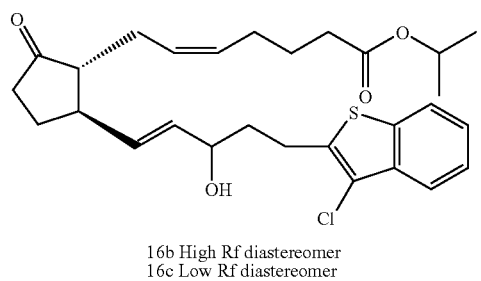

16b High Rf diastereomer
16c Low Rf diastereomer

Testing was carried out with compounds 16b and 16c, and the results are presented in Table 2.

TABLE 2

| | | | DOG | | | MONKEY |
| --- | --- | --- | --- | --- | --- | --- |
| Compound | Conc. | n | Max. ΔIOP (mm Hg) | Max hyperemia | n | Max. ΔIOP (mm Hg) |
| 16b | 0.03% | 8 | −5.7 | 0.9 | 7 | −3.4 |
| 16c | 0.03% | 8 | −4.8 | 1.0 | 10 | −7.8 |

Synthetic Procedures (3-Chloro-benzo[b]thiophen-2-yl)-methanol (2, scheme 1). To an ice cold solution of 10.0 g (47.0 mmol) of 3-chloro-benzo[b]thiophene-2-carboxylic acid (1) in 200 mL of THF was added 47 mL of LiAlH$_4$ (47 mmol, 1 M/THF). After 3 h, the reaction was quenched by addition of MeOH (ca. 40 mL). The volatiles were evaporated and the residue was treated with 50 mL 1 M HCl. After stirring for 10 min., the mixture was extracted with CH$_2$Cl$_2$ (3×150 mL). The combined CH$_2$Cl$_2$ solution was dried (MgSO$_4$), filtered and evaporated. Purification by flash chromatography on silica gel (10→20% ethyl acetate/hexane) gave 4.32 g (21.6 mmol, 46%) of the alcohol (2).

3-Chloro-benzo[b]thiophene-2-carbaldehyde (3). A solution of alcohol 2 (4.32 g, 21.6 mmol) in 40 mL of CH$_2$Cl$_2$ was treated with 4A molecular sieves, NMO (3.81 g, 32.5 mmol), and TPAP (381 mg, 1.08 mmol). The reaction was stirred for 10 min. and then was evaporated to dryness. Purification by flash chromatography on silica gel (2% ethyl acetate/hexane) gave 3.52 g (18.3 mmol, 84%) of the aldehyde (3).

(E)-3-(3-Chloro-benzo[b]thiophen-2-yl)-acrylic acid methyl ester (4). A solution of 3.52 g (18.3 mmol) of 3 in 50 mL toluene was treated with methyl(triphenylphosphoranylidene)acetate (7.48 g, 21.9 mmol). After 4 h, saturated NaHCO$_3$ solution (50 mL) was added and the mixture was extracted with ethyl acetate (2×75 mL). The combined ethyl acetate solution was washed with brine (50 mL), dried (Na$_2$SO$_4$), filtered and evaporated. Purification by flash chromatography on silica gel (5% ethyl acetate/hexane) provided 3.60 g (14.6 mmol, 80%) of the enoate (4).

3-(3-Chloro-benzo[b]thiophen-2-yl)-propionic acid methyl ester (5). A solution of 3.60 g (14.6 mmol) of 4 in 50 mL THF was treated with Wilkinson's catalyst (3.35 g, 3.62 mmol). The mixture was stirred under 1 atm H$_2$ for 18 h and then was filtered through celite. The solvent was evaporated and the residue was purified by flash chromatography on silica gel (0→2% ethyl acetate/hexane) to give 3.63 g (14.3 mmol, 99%) of the saturated ester (5).

3-(3-Chloro-benzo[b]thiophen-2-yl)-propan-1-ol (6). An ice cold solution of 3.63 g (14.3 mmol) of 5 in 60 mL of ether was treated with LiBH$_4$ (621 mg, 28.5 mmol) and methanol (2 mL). After 30 min., 30 mL of 0.5 M NaOH solution was added. The mixture was extracted with ethyl acetate (2×25 mL) and the combined ethyl acetate solution was washed with brine (50 mL), dried (MgSO$_4$), filtered and evaporated. The residue was purified by flash chromatography on silica gel (5→20% ethyl acetate/hexane) to give 2.57 g (11.3 mmol, 79%) of the alcohol (6).

3-(3-Chloro-benzo[b]thiophen-2-yl)-propionaldehyde (7). A −78° C. solution of oxalyl chloride (1.73 g, 13.6 mmol) in dichloromethane (20 mL) was treated with DMSO (20 mL). After 5 min., a solution of alcohol 6 (2.57 g, 11.3 mmol) in dichloromethane (20 mL) was added. After another 15 min., triethylamine (7.1 mL, 50.6 mmol) was added. The reaction was stirred at −78° C. for 5 min., and then was allowed to warm to room temperature. After 30 min., 100 mL water was added and the mixture was extracted with dichloromethane (3×60 mL). The combined dichloromethane solution was dried ($Na_2SO_4$), filtered and evaporated. Purification by flash chromatography on silica gel (10% ethyl acetate/hexane) gave 2.11 g (9.4 mmol, 83%) of the aldehyde (7).

5-(3-Chloro-benzo[b]thiophen-2-yl)-pent-1-yn-3-ol (8). A solution of aldehyde 7 (2.11 g, 9.4 mmol) in 15 mL THF was added to a solution of ethynylmagnesium bromide (28.2 mL, 14.1 mmol, 0.5 M THF) at 0° C. After 1.5 h, saturated $NH_4Cl$ solution (75 mL) was added and the mixture was extracted with ethyl acetate (3×50 mL). The combined ethyl acetate solution was washed with brine (50 mL) and then was dried ($Na_2SO_4$), filtered and evaporated. Purification by flash chromatography (5→20% ethyl acetate/hexane) gave 2.20 g (8.78 mmol, 93%) of the alcohol (8).

tert-Butyl-{1-[2-(3-chloro-benzo[b]thiophen-2-yl)-ethyl]-prop-2-ynyloxy}-dimethyl-silane (9). A solution of alcohol 8 (2.20 g, 8.78 mmol) in dichloromethane (15 mL) was treated with DMAP (215 mg, 1.8 mmol), TBSCl (1.59 g, 10.5 mmol), and triethylamine (1.8 mL, 13.2 mmol). The reaction was stirred for 24 h and then saturated sodium bicarbonate solution (50 mL) was added. The mixture was extracted with dichloromethane (2×50 mL) and the combined dichloromethane solution was dried ($Na_2SO_4$), filtered and evaporated. Purification by flash chromatography (4% ethyl acetate/hexane) gave 3.06 g (6.4 mmol, 73%) of the protected alcohol (9).

tert-Butyl-{(E)-1-[2-(3-chloro-benzo[b]thiophen-2-yl)-ethyl]-3-iodo-allyloxy}-dimethyl-silane (10). A solution of alkyne 9 (5.547 g, 15.2 mmol) in dichloromethane (50 mL) was treated with $Cp_2ZrHCl$ (5.794 g, 22.5 mmol). The reaction was stirred for 45 min. and then N-iodosuccinimide (4.966 g, 22.1 mmol) was added. After 15 min., saturated sodium bicarbonate solution (200 mL) was added and the mixture was extracted with dichloromethane (2×100 mL). The combined dichloromethane solution was dried ($MgSO_4$), filtered and evaporated. Purification by flash chromatography on silica gel (0%→5% ethyl acetate/hexanes) gave 6.608 g (13.1 mmol, 86%) of the vinyl iodide (10).

(Z)-7-{(1R,2R,3R)-3-(tert-Butyl-dimethyl-silanyloxy)-2-[(E)-3-(tert-butyl-dimethyl-silanylox)-5-(3-chloro-benzo[b]thiophen-2-yl)-pent-1-enyl]-5-oxo-cyclopentyl}-hept-5-enoic acid methyl ester (12, scheme 2). A −78° C. solution of iodide 10 (scheme 2, 2.305 g, 4.6 mmol) in THF (10 mL) was treated dropwise with t-butyllithium (5.9 mL, 10.0 mmol, 1.7 M/pentane). After stirring for 30 minutes, the red mixture was treated with lithium 2-thienylcyanocuprate (18.4 mL, 4.6 mmol, 0.25 M/THF, Aldrich). The resulting brown mixture was stirred in an ice bath for 10 minutes and then was cooled back down to −78° C. At this time, a solution of enone 11 (1.63 g, 4.6 mmol) in THF (5.0 mL) was added dropwise by cannula and the resulting mixture was stirred for 30 minutes at −78° C., 30 minutes at 0° C. and then 30 min. at room temperature.

The reaction was quenched by addition of a solution of 10 mL concentrated $NH_4OH$ in 90 mL saturated $NH_4Cl$. The resulting mixture was stirred for 15 min. and was then extracted with ethyl acetate (3×100 mL). The combined ethyl acetate solution was dried ($MgSO_4$), filtered, and evaporated. Purification by flash chromatography on silica gel (10% ethyl acetate/hexanes) provided the title ketone 12 (1.781 g, 2.5 mmol, 54%).

(Z)-7-{(1R,2S)-2-[(E)-3-(tert-Butyl-dimethyl-silanyloxy)-5-(3-chloro-benzo[b]thiophen-2-yl)-pent-1-enyl]-5-oxo-cyclopent-3-enyl}-hept-5-enoic acid methyl ester (13). A solution of ketone 12 (1.781 g, 2.5 mmol) in acetic acid (24 mL)/$H_2O$ (12 mL)/THF (12 mL) was heated at 70° C. (bath temperature) for 16 h. The solution was allowed to cool to room temperature and then was poured into 750 mL saturated $NaHCO_3$ solution. The mixture was extracted with ethyl acetate (4×200 mL) and the combined ethyl acetate solution was dried ($Na_2SO_4$), filtered and evaporated. Purification by flash chromatography on silica gel (50% ethyl acetate/hexanes) gave 0.686 g (1.5 mmol, 60%) of the C15 free alcohol version of C15 silyl ether 13.

A solution of the above C15 alcohol in dichloromethane (8 mL) was treated with 2,6-lutidine (0.20 mL, 1.7 mmol) and TBSOTf (0.37 mL, 1.6 mmol). After 1 h, saturated $NaHCO_3$ was added and the resulting mixture extracted with dichloromethane (3×25 mL). The combined dichloromethane solution was washed with 1 M HCl (50 mL) and brine (50 mL) and then was dried ($Na_2SO_4$), filtered and evaporated. Purification by flash chromatography on silica gel (10% ethyl acetate/hexanes) gave the title enone 13 (706 mg, 1.2 mmol, 83%).

(Z)-7-{(1R,2R)-2-[(E)-3-(tert-Butyl-dimethyl-silanyloxy)-5-(3-chloro-benzo[b]thiophen-2-yl)-pent-1-enyl]-5-oxo-cyclopentyl}-hept-5-enoic acid methyl ester (14, R=H). A solution of enone 13 (145 mg, 0.25 mmol) in toluene (4 mL) was added to a −45° C. mixture of $[Ph_3PCuH]_6$ in toluene (4 mL), rinsing with 0.5 mL toluene. The mixture was allowed to stir for 1 h and then was allowed to warm to room temperature. After 19 h at room temperature, the reaction was quenched by addition of 15 mL saturated $NH_4Cl$ solution. The resulting mixture was extracted with ethyl acetate (3×15 mL) and the combined ethyl acetate solution was dried ($Na_2SO_4$), filtered and evaporated. Purification by flash chromatography on silica gel (7.5% ethyl acetate/hexanes→12.5%) gave ketone 14 (R=H, 111 mg, 0.19 mmol, 76%).

(Z)-7-{(1R,2R,3R)-2-[(E)-3-(tert-Butyl-dimethyl-silanyloxy)-5-(3-chloro-benzo[1b]thiophen-2-yl)-pent-1-enyl]-3-methyl-5-oxo-cyclopentyl}-hept-5-enoic acid methyl ester 14 (R=methyl). A −78° C. mixture of CuCN (47 mg, 0.52 mmol) in 0.5 mL THF was treated with methyllithium (0.57 mL, 0.80 mmol, 1.4 M/ether). The reaction was stirred for 5 minutes at −78° C. and then for 10 min. at room temperature. The reaction was cooled back down to −78° C. and then a solution of enone 13 (80 mg, 0.14 mmol) in 0.5 mL THF was added by cannula, rinsing with 0.2 mL THF. The reaction was stirred for 2 h at −78° C. and then 10 mL saturated ammonium chloride solution was added. The resulting mixture was stirred for 20 min. at room temperature and then was extracted with dichloromethane (3×15 mL). The combined dichloromethane solution was dried ($Na_2SO_4$), filtered and evaporated to leave the title compound.

(Z)-7-{(1R,2R,3R)-2-[(E)-3-(tert-Butyl-dimethyl-silanyloxy)-5-(3-chloro-benzo[b]thiophen-2-yl)-pent-1-enyl]-3-ethyl-5-oxo-cyclopentyl}-hept-5-enoic acid methyl ester 14 (R=Et). A 0° C. mixture of CuI (77 mg, 0.4 mmol) in 0.2 mL THF was treated with ethylmagnesium bromide (0.72 mL, 0.72 mmol, 1 M/THF). After 5 min., the grey mixture was cooled to −78° C. and a solution of enone 13 (67 mg, 0.11 mmol) in 0.5 mL THF was added by cannula, rinsing with 0.25 mL THF. After 45 min., saturated ammonium chloride solution was added. The resulting mixture was stirred for 15 min. and then was extracted with ethyl acetate (3×15 mL). The combined ethyl acetate solution was dried ($Na_2SO_4$), filtered and evaporated. Purification by flash chromatography on silica gel (5% ethyl acetate/hexanes→7.5%) gave the title compound (31 mg, 0.05 mmol, 46%). A similar procedure was used to prepare 14 (R=iPr, vinyl).

(Z)-7-{(1R,2R,3R)-2-[(E)-5-(3-Chloro-benzo[b]thiophen-2-yl)-3-hydroxy-pent-1-enyl]-3-ethyl-5-oxo-cyclopentyl}-hept-5-enoic acid methyl ester 15 (R=Et). A solution of 14 (R=Et, 31 mg, 0.05 mmol) in acetonitrile (1 mL) was treated with HF-pyridine (0.19 mL). After 4 h, the reaction was poured into 20 mL of saturated $NaHCO_3$ solution. The resulting mixture was extracted with dichloromethane (3×15 mL) and the combined dichloromethane solution was dried ($Na_2SO_4$), filtered and evaporated. Purification by flash chromatography (25% ethyl acetate/hexanes) gave the title compound (18 mg, 0.035 mmol, 71%). Compounds 15 (R=H, Me, iPr, vinyl) were prepared in a similar way. In the case of 15 (R=H), the C15 diastereomers were separated by preparative TLC on silica gel (30% ethyl acetate/hexanes).

(Z)-7-{(1R,2R,3R)-2-[(E)-5-(3-Chloro-benzo[b]thiophen-2-yl)-3-hydroxy-pent-1-enyl]-3-ethyl-5-oxo-cyclopentyl}-hept-5-enoic acid 16a (R=Et). A solution of ester 15 (R=Et, 10 mg, 0.020 mmol), 0.5 M LiOH (0.10 mL, 0.05 mmol) and THF (0.7 mL) was stirred at room temperature for 17 h. HCl (10 mL, 1 M) was added and the resulting mixture was extracted with dichloromethane (3×15 mL). The combined dichloromethane solution was then dried ($Na_2SO_4$), filtered and evaporated. Purification by flash chromatography on silica gel (2% methanol/dichloromethane→5%) gave the title acid (9 mg, 0.018 mmol, 92%). 300 MHz $^1H$ NMR ($CDCl_3$, ppm) δ 7.73 (2 H, d, J=8.0 Hz) 7.4–7.3 (2H, m) 5.7–5.3 (4H, m) 4.3–4.2 (1H, m) 3.1–3.0 (2 H, m) 2.6–1.1 (17H, overlapping m) 0.94–0.85 (3H, m). The other acids 16a (R=H, Me, iPr, vinyl) were prepared in a similar way.

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid isopropyl ester; general procedure for isopropyl ester formation (16b, R=H, high Rf diastereomer). An acetone (0.2 mL) solution of 16a (R=H, high Rf diastereomer, 6 mg, 0.013 mmol), DBU (4 µL, 0.027 mmol) and 2-iodopropane (20 µL, 0.20 mmol) was stirred at room temperature for 4 days. HCl (10 mL, 1 M) was added and the resulting mixture was extracted with dichloromethane (3×15 mL). The combined dichloromethane solution was dried ($Na_2SO_4$), filtered and evaporated. The residue was purified by flash chromatography on silica gel (30% ethyl acetate/hexanes) to give the title compound (6 mg, 0.012 mmol, 92%).

tert-Butyl-hex-5-ynyloxy-dimethyl-silane (18, scheme 3). A solution of 5-hexyn-1-ol (17, 5.20 g, 0.053 mmol), imidazole (7.2 g, 0.106 mmol) and TBSCl (11.8 g, 0.079 mmol) in DMF (53 mL) was stirred for 12 h. The reaction was diluted with ether and washed with 1 M HCl, saturated aqueous sodium bicarbonate, and brine. The solution was then dried ($MgSO_4$), filtered and concentrated in vacuo. Purification by flash chromatography on silica gel (19:1 hexane/ethyl acetate) gave 8.65 g (77%) of 18.

7-(tert-Butyl-dimethyl-silanyloxy)-hept-2-yn-1-ol (19). n-butyllithium (15.3 mL, 0.025 mmol, 1.6 M/hexane) was added to a solution of 18 (5.0 g, 0.024 mmol) in THF (48 mL) at −10° C. After 0.5 h at 0° C., the reaction was recooled to −10° C. and paraformaldehyde (1.06 g, 0.035 mmol) was added. The reaction was allowed to warm to 23° C., stirred for 16 h and then was quenched by addition of saturated aqueous ammonium chloride. The reaction ws extracted with ethyl acetate and the organic portion was washed with brine. The solution was then dried ($MgSO_4$), filtered and concentrated in vacuo. Purification by flash chromatography on silica gel (4:1 hexane/ethyl acetate) gave 3.0 g (52%) of 19.

Acetic acid 7-(tert-butyl-dimethyl-silanyloxy)-hept-2-ynyl ester (20). A solution of 7-(tert-Butyl-dimethyl-silanyloxy)-hept-2-yn-1-ol 19 (4.507 g, 21 mmol) in pyridine (20 mL) was treated with acetic anhydride (3.0 mL, 31.8 mmol). After 18 h, the solvent was evaporated and the residue co-evaporated with toluene. The residue was used directly in the next step.

7-Acetoxy-hept-5-ynoic acid (21). A solution of crude 20 in acetone (100 mL) was treated with Jones Reagent (18.0 mL, 41.4 mmol, 2.3 M). The mixture became warm and so was cooled with an ice bath. After 1 h at room temperature, 10 mL isopropyl alcohol was added and the mixture stirred further for 15 min. The mixture still had a brown color so another 10 mL isopropyl alcohol was added. After another 15 min., the color had not changed so the mixture was filtered through celite and the filtrate evaporated in vacuo. The residue was partitioned between 100 mL ether and 100 mL saturated ammonium chloride solution. The aqueous layer was extracted with 100 mL ether and the combined ether solution washed with brine and then was dried ($MgSO_4$), filtered and evaporated to leave a yellow oil (21, 6.333 g) that was used directly in the next step.

7-Hydroxy-hept-5-ynoic acid methyl ester (22). The crude acid 21 (6.333 g) was treated with a 1% solution of acetyl chloride in methanol (60 mL). After 16 h, sodium bicarbonate (1.966 g, 23.4 mmol) was added. The mixture was dried ($MgSO_4$), filtered through celite and evaporated in vacuo. Purification by flash chromatography on silica gel (30–40% ethyl acetate/hexanes) gave 7-Hydroxy-hept-5-ynoic acid methyl ester 22 (3.022 g, 19.3 mmol, 92% from 7-(tert-Butyl-dimethyl-silanyloxy)-hept-2-yn-1-ol 20).

7-Iodo-hept-5-ynoic acid methyl ester (23). A solution of 22 (1.347 g, 8.6 mmol) in 5 mL dichloromethane was added to a mixture of triphenylphosphine (2.725 g, 10.4 mmol), imidazole (726 mg, 10.7 mmol), and iodine (2.602 g, 10.3 mmol) in 34 mL dichloromethane, rinsing with 5 mL dichloromethane. After 40 min., the dichloromethane was evaporated in vacuo to a few mL's and the resulting mixture filtered through basic alumina, washing with 10% ethyl acetate/hexanes. Purification by flash chromatography on silica gel (10% ethyl acetate/hexanes) gave 23 (1.878 g, 7.1 mmol, 83%) of the propargyl iodide.

7-[(1R,2S,3R)-2-[(E)-3-(tert-Butyl-dimethyl-silanyloxy)-5-(3-chloro-benzo[b]thiophen-2-yl)-pent-1-enyl]-3-(tert-butyl-dimethyl-silanyloxymethyl)-5-oxo-cyclopentyl]-hept-5-ynoic acid methyl ester (25). A −78° C. solution of iodide 10 (2.194 g, 4.45 mmol) in THF (5.0 mL) was treated with tert-butyllithium (5.2 mL, 8.84 mmol), 1.7 M/pentane). The dark brown mixture was stirred for 30 min. and then dimethylzinc (2.2 mL, 4.4 mmol, 2 M/toluene) was added. The solution was stirred at 0° C. for 15 min. and then recooled to −78° C. At this time, a solution of enone 24 (508 mg, 2.24 mmol) in THF (3.0 mL) was added over 1 h by syringe pump, rinsing with 0.5 mL THF. After 30 min., HMPA (3.8 mL, 21.8 mmol) was added followed by a solution of propargyl iodide 23 (2.379 g, 8.9 mmol) in THF (3.0 mL). The solution was stirred in a −40° C. bath for 19 h and then the reaction was quenched by addition of 50 mL saturated ammonium chloride solution. The mixture was extracted with ethyl acetate (3×75 mL) and the combined organic extracts were dried ($Na_2SO_4$), filtered and evaporated. Purification by flash chromatography on silica gel (2→8% ethyl acetate/hexanes) gave 136 mg (0.18 mmol, 8%) of 25.

7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-ynoic acid methyl ester (26, 27). A solution of 25 (136 mg, 0.18 mmol) in $CH_3CN$ (3 mL) was treated with HF-pyridine (1 mL). The solution was stirred for 3 h and saturated sodium bicarbonate solution (100 mL) was added. The mixture was extracted with dichloromethane (3×60 mL) and the combined dichloromethane solution was dried ($Na_2SO_4$), filtered and evaporated. Purification by flash chromatography (50% ethyl acetate/hexane→55%→60%→75%) gave 15 mg (0.03 mmol, 16%) of the less polar diastereomer (26) and 16 mg (0.03 mmol, 16%) of the more polar diastereomer (27).

(Z)-7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-enoic acid methyl ester (28, 29). A mixture of $NaBH_4$ (6 mg, 0.17 mmol) and $NiCl_2$ (57 mg, 0.43 mmol) was treated with 95% ethanol (1 mL). The resulting mixture was stirred for 5 min. and then ethylenediamine (50 μL, 0.75 mmol) was added. After 15 min., a solution of 26 (15 mg) in 95% ethanol (1 mL) was added by cannula. The mixture was stirred under 1 atm $H_2$ (balloon) overnight. The mixture was then filtered through Celite and evaporated. Purification of the residue by flash chromatography on silica gel (4% methanol/dichloromethane) followed by preparative TLC (6% methanol/dichloromethane) gave 28 (7 mg, 0.014 mmol, 46%). The more polar diastereomer 27 was converted to 29 using a similar procedure.

(Z)-7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-enoic acid (30, 31). A solution of 28 (6 mg, 0.011 mmol) and rabbit liver esterase (1 mg) in pH 7.2 phosphate buffer (1 mL)/$CH_3CN$ (0.08 mL) was stirred for 17 h. The mixture was then coevaporated with $CH_3CN$ to remove water. The residue was purified by flash chromatography on silica gel (5% MeOH/$CH_2Cl_2$) followed by preparative TLC (5% MeOH/$CH_2Cl_2$) to give 5 mg (0.010 mmol, 93%) of the acid (30). The other diastereomer 31 was prepared by a similar procedure.

2-Benzo[b]thiophen-2-yl-ethanol (33, scheme 5). n-BuLi (100 mL, 160 mmol, 1.6M/hexanes) was added to a −78° C. mixture of thianaphthene (17.31 g, 129 mmol) in THF (70 mL)/ether (30 mL). The mixture was stirred at −78° C. for 2 h and then a solution of ethylene oxide (42.86 g, 1.071 mmol) in THF (70 mL)/ether (30 mL) was added by cannula over 15 min. The resulting mixture was stirred for 2 h at −78° C. and then at room temperature for 15 h. At this time, the mixture was evaporated, 200 mL $H_2O$ was added, and the resulting mixture was extracted with ethyl acetate (3×150 mL). The combined organic solution was washed with brine and then was dried ($Na_2SO_4$), filtered, and evaporated. Purification by flash chromatography on silica gel (20% ethyl acetate/hexanes) gave 33 (13.61 g, 78 mmol, 60%).

Benzo[b]thiophen-2-yl-acetaldehyde (34). A 0° C. mixture of 33 (8.019 g, 44.9 mmol) in 100 mL dichloromethane was treated with Dess-Martin reagent (20 g, 47.2 mmol). The mixture was stirred at 0° C. for 10 min. and at room temperature for 40 min. Saturated $NaHCO_3$ solution (200 mL) and 0.1 M $NaHSO_3$ solution were added and the resulting mixture was extracted with ethyl acetate (3×300 mL). The combined organic solution was dried ($Na_2SO_4$), filtered and evaporated to give 34 (8.77 g). The aldehyde was taken on crude for the next reaction.

1-Benzo[b]thiophen-2-yl-but-3-yn-2-ol (35). A solution of crude 34 (8.77 g) in THF (100 mL) was added to a solution of ethynylmagnesium bromide (450 mL, 225 mmol, 0.5 M/THF) at 0° C. by cannula. The mixture was stirred for 1 h at 0° C. and for 1 h at room temperature. The reaction was then queched by addition of 200 mL saturated $NH_4Cl$ solution. The layers were separated and the aqueous layer was extracted with ethyl acetate (3×200 mL). The combined organic solution was washed with brine and then was dried ($Na_2SO_4$), filtered and evaporated. Purification by flash chromatography on silica gel (10%→20% ethyl acetate/hexanes) gave 35 (7.67 g, 37.9 mmol, 84% from 33).

(1-Benzo[b]thiophen-2-ylmethyl-prop-2-ynyloxy)-tert-butyl-dimethyl-silane (36). DMAP (2.306 g, 18.9 mmol), TBSCl (11.502 g, 76.3 mmol) and triethylamine (5.25 mL, 37.7 mmol) were added to a solution of 35 (7.67 g, 37.9 mmol) in dichloromethane (120 mL). After 17 h, 150 mL of saturated $NH_4Cl$ solution was added and the layers were separated. The aqueous layer was extracted with dichloromethane (3×100 mL) and the combined organic solution was dried ($Na_2SO_4$), filtered and evaporated. Purification by flash chromatography on silica gel (4% ethyl acetate/hexanes) gave 36 (8.38 g, 26.5 mmol, 70%).

((E)-1-Benzo[b]thiophen-2-ylmethyl-3-iodo-allyloxy)-tert-butyl-dimethyl-silane (37). $Cp_2ZrHCl$ (1.719 g, 6.67 mmol) was added to a solution of 36 (1.372 g, 4.34 mmol) in dichloromethane (30 mL). The reaction was stirred for 30 min. at room temperature and N-iodosuccinimide (1.997 g, 8.88 mmol) was added. After 1 h, the reaction was poured into 100 mL of saturated $NaHCO_3$ solution. The resulting mixture was extracted with dichloromethane (3×75 mL) and the combined organic extracts were dried ($Na_2SO_4$), filtered and evaporated. Purification by flash chromatography on silica gel (2% ethyl acetate/hexanes) gave 37 (1.7484 g, 91%).

Compounds 38–41 were prepared in an analogous sequence to that of 30,31 using the bottom chain vinyl iodide 37 (scheme 5) as the starting material.

Names not already in exptl:

(Z)-7-{(1R,2S,3S)-2-[(E)-5-(3-Chloro-benzo[b]thiophen-2-yl)-3-hydroxy-pent-1-enyl]-3-isopropyl-5-oxo-cyclopentyl}-hept-5-enoic acid methyl ester (15, R=iPr).

(Z)-7-{(1R,2R,3R)-2-[(E)-5-(3-Chloro-benzo[b]thiophen-2-yl)-3-hydroxy-pent-1-enyl]-3-methyl-5-oxo-cyclopentyl}-hept-5-enoic acid methyl ester (15, R=Me).

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid methyl ester (15, R=H).

(Z)-7-{(1R,2S,3S)-2-[(E)-5-(3-Chloro-benzo[b]thiophen-2-yl)-3-hydroxy-pent-1-enyl]-5-oxo-3-vinyl-cyclopentyl}-hept-5-enoic acid methyl ester (15, R=vinyl).

(Z)-7-{(1R,2S,3S)-2-[(E)-5-(3-Chloro-benzo[b]thiophen-2-yl)-3-hydroxy-pent-1-enyl]-3-isopropyl-5-oxo-cyclopentyl}-hept-5-enoic acid (16a, R=iPr).

(Z)-7-{(1R,2R,3R)-2-[(E)-5-(3-Chloro-benzo[b]thiophen-2-yl)-3-hydroxy-pent-1-enyl]-3-methyl-5-oxo-cyclopentyl}-hept-5-enoic acid (16a, R=Me).

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid (16a, R=H).

(Z)-7-{(1R,2S,3S)-2-[(E)-5-(3-Chloro-benzo[b]thiophen-2-yl)-3-hydroxy-pent-1-enyl]-5-oxo-3-vinyl-cyclopentyl}-hept-5-enoic acid (16a, R=vinyl).

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid isopropyl ester (16b, R=H).

(Z)-7-[(1R,2S,3R)-2-((E)-4-Benzo[b]thiophen-2-yl-3-hydroxy-but-1-enyl)-3-hydroxymethyl-5-oxo-cyclopentyl]-hept-5-enoic acid methyl ester (38,39)

(Z)-7-[(1R,2S,3R)-2-((E)-4-Benzo[b]thiophen-2-yl-3-hydroxy-but-1-enyl)-3-hydroxymethyl-5-oxo-cyclopentyl]-hept-5-enoic acid (40,41).

Compounds 38–41 were prepared in an analogous sequence to that of 30,31 using the bottom chain vinyl iodide 37 (scheme 5) as the starting material.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

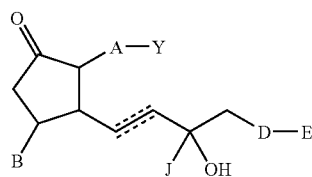

or a pharmaceutically acceptable salt or a prodrug thereof, wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is —$(CH_2)_6$—, cis —$CH_2$—CH=CH—$(CH_2)_3$—, or —$CH_2$—C≡C—$(CH_2)_3$— wherein 1 or 2 carbons may be substituted with S or O;

B is hydrogen, $C_{1-6}$ hydrocarbyl, CN, $CO_2H$, or —$(CH_2)_m$X$(CH_2)_p$H, wherein m is at least 1 and the sum of m and p is from 1 to 5;

X is S or O;

J is H, $CH_3$, or $CF_3$;

D is a covalent bond, $CH_2$, O, or S; and

E is an aromatic heterobicyclic ring system which may have substituents comprising up to 6 non-hydrogen atoms each.

2. The compound of claim 1 wherein B is hydrocarbyl having from 1 to 3 carbon atoms.

3. The compound of claim 2 wherein B is ethyl.

4. The compound of claim 2 wherein B is methyl.

5. The compound of claim 2 wherein B is ethenyl.

6. The compound of claim 1 wherein B is hydrogen.

7. The compound of claim 1 wherein D is $CH_2$.

8. The compound of claim 1 of the formula

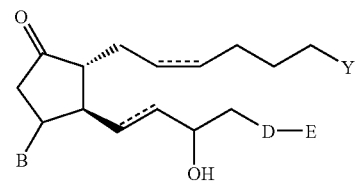

or a pharmaceutically acceptable salt or a prodrug thereof.

9. The compound of claim 8 wherein D is $CH_2$.

10. The compound of claim 8 wherein D is S or O.

11. The compound of claim 1 wherein E is benzothienyl having from 0 to 3 substituents, said substituents comprising no more than 4 non-hydrogen atoms each.

12. The compound of claim 11 wherein E is a monosubstituted benzothienyl.

13. The compound of claim 12 wherein E is 3-chloro-2-benzothienyl.

14. The compound of claim 2 of the formula

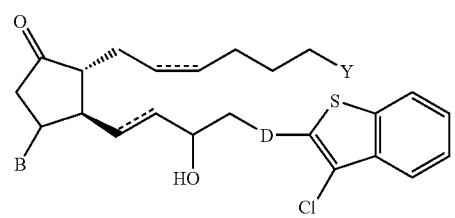

or a pharmaceutically acceptable salt or a prodrug thereof.

15. The compound of claim 1 selected from the group consisting of (Z)-7-{(1R,2R,3R)-2-[(E)-5-(3-Chloro-benzo[b]thiophen-2-yl)-3-hydroxy-pent-1-enyl]-3-ethyl-5-oxo-cyclopentyl}-hept-5-enoic acid methyl ester;

(Z)-7-{(1R,2R,3R)-2-[(E)-5-(3-Chloro-benzo[b]thiophen-2-yl)-3-hydroxy-pent-1-enyl]-3-ethyl-5-oxo-cyclopentyl}-hept-5-enoic acid;

7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-ynoic acid methyl ester;

(Z)-7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-enoic acid methyl ester;

(Z)-7-{(1R,2S,3R)-2-[(E)-5-(3-Chloro-benzo[b]thiophen-2-yl)-3-hydroxy-pent-1-enyl]-3-hydroxymethyl-5-oxo-cyclopentyl}-hept-5-enoic acid;

(Z)-7-{(1R,2S,3S)-2-[(E)-5-(3-Chloro-benzo[b]thiophen-2-yl)-3-hydroxy-pent-1-enyl]-3-isopropyl-5-oxo-cyclopentyl}-hept-5-enoic acid methyl ester;

(Z)-7-{(1R,2R,3R)-2-[(E)-5-(3-Chloro-benzo[b]thiophen-2-yl)-3-hydroxy-pent-1-enyl]-3-methyl-5-oxo-cyclopentyl}-hept-5-enoic acid methyl ester;

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid methyl ester;

(Z)-7-{(1R,2S,3S)-2-[(E)-5-(3-Chloro-benzo[b]thiophen-2-yl)-3-hydroxy-pent-1-enyl]-5-oxo-3-vinyl-cyclopentyl}-hept-5-enoic acid methyl ester;

(Z)-7-{(1R,2S,3S)-2-[(E)-5-(3-Chloro-benzo[b]thiophen-2-yl)-3-hydroxy-pent-1-enyl]-3-isopropyl-5-oxo-cyclopentyl}-hept-5-enoic acid;

(Z)-7-{(1R,2R,3R)-2-[(E)-5-(3-Chloro-benzo[b]thiophen-2-yl)-3-hydroxy-pent-1-enyl]-3-methyl-5-oxo-cyclopentyl}-hept-5-enoic acid;

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid;

(Z)-7-{(1R,2S,3S)-2-[(E)-5-(3-Chloro-benzo[b]thiophen-2-yl)-3-hydroxy-pent-1-enyl]-5-oxo-3-vinyl-cyclopentyl}-hept-5-enoic acid;

(Z)-7-[(1R,2S,3R)-2-((E)-4-Benzo[b]thiophen-2-yl-3-hydroxy-but-1-enyl)-3-hydroxymethyl-5-oxo-cyclopentyl]-hept-5-enoic acid methyl ester;

(Z)-7-{(1R,2R)-2-[(E)-5-(3-Chloro-benzo[b]thiophen-2-yl)-3-hydroxy-pent-1-enyl]-5-oxo-cyclopentyl}-hept-5-enoic acid isopropyl ester; and (Z)-7-[(1R,2S,3R)-2-((E)-4-Benzo[b]thiophen-2-yl-3-hydroxy-but-1-enyl)-3-hydroxymethyl-5-oxo-cyclopentyl]-hept-5-enoic acid.

16. A liquid pharmaceutical composition comprising a compound, wherein said liquid is formulated for ophthalmic administration, said compound comprising

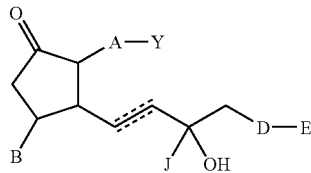

or a pharmaceutically acceptable salt or a prodrug thereof, wherein
  a dashed line represents the presence or absence of a bond;
  Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;
  A is —$(CH_2)_6$—, cis —$CH_2$—CH=CH—$(CH_2)_3$—, or —$CH_2$—C≡C—$(CH_2)_3$— wherein 1 or 2 carbons may be substituted with S or O;
  B is hydrogen, $C_{1-6}$ hydrocarbyl, CN, $CO_2H$, or —$(CH_2)_m$X$(CH_2)_p$H, wherein m is at least 1 and the sum of m and p is from 1 to 5;
  X is S or O;
  J is H, $CH_3$, or $CF_3$;
  D is a covalent bond, $CH_2$, O, or S; and
  E is an aromatic heterobicyclic ring system which may have substituents comprising up to 6 non-hydrogen atoms each.

17. A method comprising administering a compound to a mammal for the treatment of glaucoma or ocular hypertension, said compound comprising

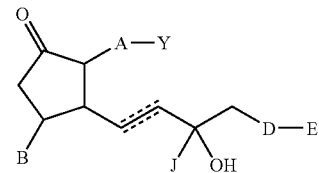

or a pharmaceutically acceptable salt or a prodrug thereof, wherein
  a dashed line represents the presence or absence of a bond;
  Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;
  A is —$(CH_2)_6$—, cis —$CH_2$—CH=CH—$(CH_2)_3$—, or —$CH_2$—C≡C—$(CH_2)_3$— wherein 1 or 2 carbons may be substituted with S or O;
  B is hydrogen, $C_{1-6}$ hydrocarbyl, CN, $CO_2H$, or —$(CH_2)_m$X$(CH_2)_p$H, wherein m is at least 1 and the sum of m and p is from 1 to 5;
  X is S or O;
  J is H, $CH_3$, or $CF_3$;
  D is a covalent bond, $CH_2$, O, or S; and
  E is an aromatic heterobicyclic ring system which may have substituents comprising up to 6 non-hydrogen atoms each.

18. A pharmaceutical product, comprising a container adapted to dispense a compound in an ophthalmic liquid from said container in metered form; said compound comprising

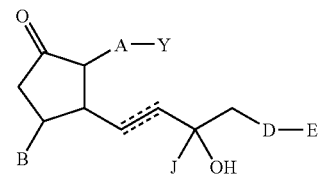

or a pharmaceutically acceptable salt or a prodrug thereof, wherein
  a dashed line represents the presence or absence of a bond;
  Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;
  A is —$(CH_2)_6$—, cis —$CH_2$—CH=CH—$(CH_2)_3$—, or —$CH_2$—C≡C—$(CH_2)_3$— wherein 1 or 2 carbons may be substituted with S or O;
  B is hydrogen, $C_{1-6}$ hydrocarbyl, CN, $CO_2H$, or —$(CH_2)_m$X$(CH_2)_p$H, wherein m is at least 1 and the sum of m and p is from 1 to 5;
  X is S or O;
  J is H, $CH_3$, or $CF_3$;
  D is a covalent bond, $CH_2$, O, or S; and
  E is an aromatic heterobicyclic ring system which may have substituents comprising up to 6 non-hydrogen atoms each.

19. The compound of claim 1 wherein J is H.

20. The compound of claim 1 wherein Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and tetrazolyl-$R^2$;

wherein $R^2$ is independently H, $C_1$–$C_6$ alkyl, phenyl, or biphenyl.

21. The compound of claim 1 wherein B is $CH_2OH$.

22. The compound of claim 21 of the formula

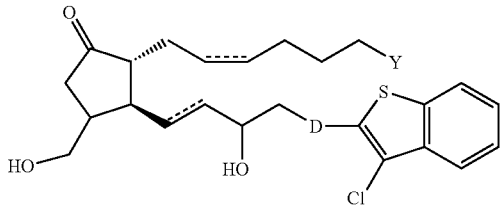

or a pharmaceutically acceptable salt or a prodrug thereof.

23. The compound of claim 22 wherein D is $CH_2$.

24. A method comprising administering a compound to a mammal suffering from an inflammatory bowel disease for the treatment of said disease, said compound comprising

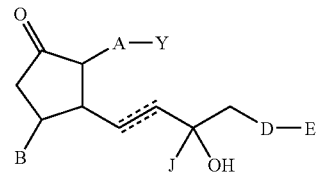

or a pharmaceutically acceptable salt or a prodrug thereof, wherein
a dashed line represents the presence or absence of a bond;
Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;
A is —$(CH_2)_6$—, cis —$CH_2$—CH=CH—$(CH_2)_3$—, or —$CH_2$—C≡C—$(CH_2)_3$— wherein 1 or 2 carbons may be substituted with S or O;
B is hydrogen, $C_{1-6}$ hydrocarbyl, CN, $CO_2H$, or —$(CH_2)_m$X$(CH_2)_p$H, wherein m is at least 1 and the sum of m and p is from 1 to 5;
X is S or O;
J is H, $CH_3$, or $CF_3$;
D is a covalent bond, $CH_2$, O, or S; and
E is an aromatic heterobicyclic ring system which may have substituents comprising up to 6 non-hydrogen atoms each.

* * * * *